United States Patent [19]

Orton

[11] 4,108,175
[45] Aug. 22, 1978

[54] CATHETER INSERTION APPARATUS

[76] Inventor: Dale W. Orton, 9716 Laurel St., Omaha, Nebr. 68134

[21] Appl. No.: 763,706

[22] Filed: Jan. 28, 1977

[51] Int. Cl.² .............................................. A61M 5/00
[52] U.S. Cl. .................................. 128/214.4; 128/2 F; 128/216; 128/278
[58] Field of Search .............. 128/2 F, DIG. 5, 214.4, 128/216, 221, 278, 231, 232

[56] References Cited

U.S. PATENT DOCUMENTS

| 2,594,621 | 4/1952 | Derrick | 128/278 |
| 2,771,879 | 11/1956 | Salisbury | 128/216 |
| 3,405,706 | 10/1968 | Cinqualbre | 128/2 F |
| 3,459,183 | 8/1969 | Ring et al. | 128/2 F X |
| 3,599,637 | 8/1971 | Schwartz | 128/214.4 |
| 3,714,945 | 2/1973 | Stanley | 128/214.4 |

Primary Examiner—Dalton L. Truluck
Attorney, Agent, or Firm—H. Gordon Shields

[57] ABSTRACT

Apparatus is disclosed for inserting a catheter into a vein and for withdrawing a positive supply of blood from the vein to insure that the catheter is inserted into the vein by providing a reduction in pressure below atmospheric pressure in a chamber in the catheter insertion apparatus in which the reduction in pressure is accomplished by using the thumb of the hand used to insert the apparatus into the vein.

10 Claims, 17 Drawing Figures

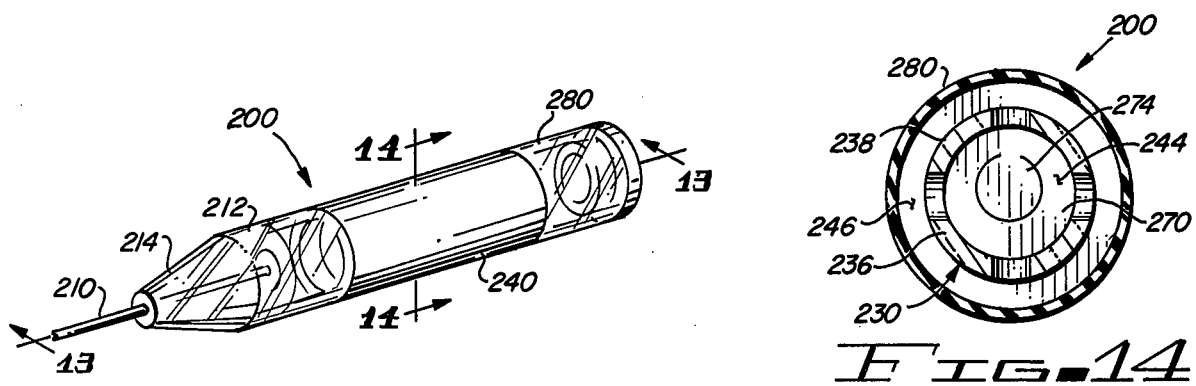
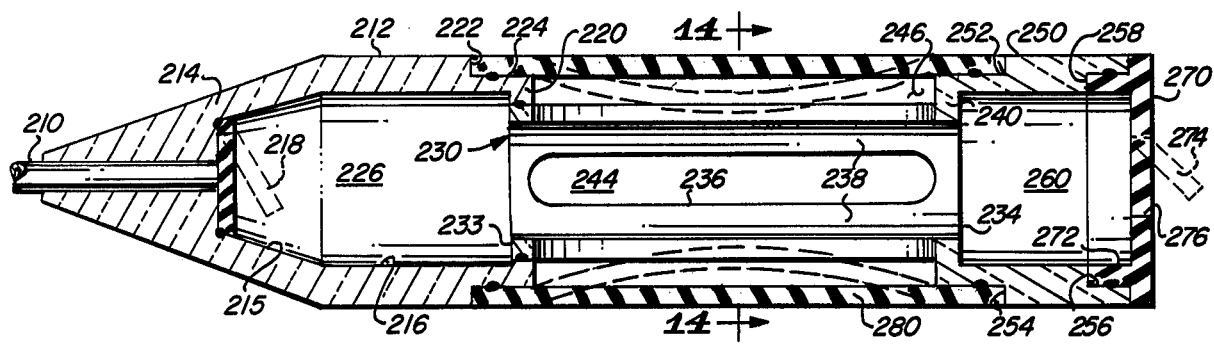
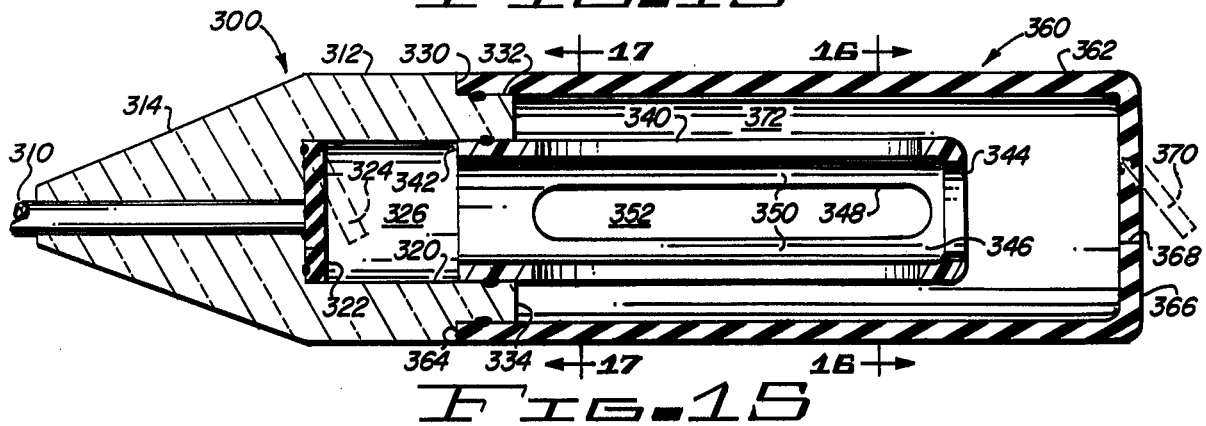
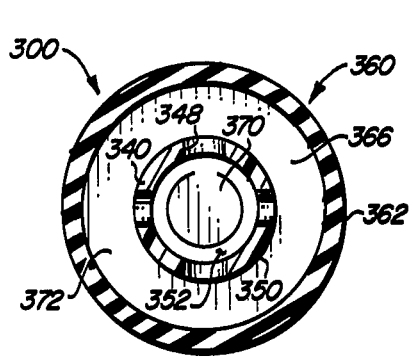
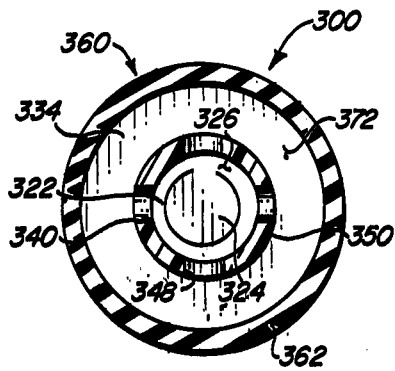

CATHETER INSERTION APPARATUS

BACKGROUND OF THE INVENTION

1. Field of the Invention

This invention relates to apparatus for inserting a catheter into a vein, and, more particularly, to apparatus for inserting a catheter into a vein by using a single hand to guide and insert the apparatus and to use the thumb of the same guiding hand to reduce pressure in a chamber in the catheter insertion apparatus below atmospheric pressure to withdraw a sample of blood from the vein to insure that the catheter is properly inserted.

2. Description of the Prior Art

Catheters are used to administer fluids to a patient by inserting a catheter into a vein of a patient as an "indwelling" element to which fluid supplies may be secured. The catheters are connected to the supply of fluids for introduction of the fluids into the individual over a relatively long period of time. The catheter is typically made of metal or of a polymerized resin, such as polytetrafluoroethylene, polypropylene, polyethylene, or similar synthetic material.

Once the catheter is inserted into a vein, it is left in the vein for fluid insertion for as long a period of time as is practical or as required. In most cases, the length of time a catheter is left in a vein depends on the condition of the vein, which in turn is a reflection upon the age of the patient, the medical problem, and other factors. Over a period of time, a vein rejects the catheter by inflammation and clotting. This is a typical body reaction to the insertion of a foreign element.

A catheter is inserted into a vein in conjunction with, or by, a catheter insertion device which is typically a relatively long metal needle used to pierce a vein. There are primarily two types of such catheter insertion devices. One type is an internal piercing device which is disposed within a catheter and the catheter accordingly comprises an external sleeve. The second type is an external sleeve in which the catheter is disposed within the needle. The first type is more common than the second type.

After the needle and catheter have been inserted into a vein (venipuncture), the proper insertion must be confirmed by withdrawing a sample of blood from the vein. In a substantial number of times, usually about fifty percent, the needle and catheter are not properly inserted into a vein. Rather, the needle and catheter are either disposed outside of a vein or else they penetrate through a vein and into tissue about the vein. With respect to a catheter insertion apparatus of the first type, if improper insertion is made, the apparatus may be withdrawn, flushed, and reused to insert the catheter. Of the second type, where the catheter is inserted within the piercing instrument or needle, the apparatus is usually not flushed and reused, but rather a new apparatus is used for a second or subsequent try at appropriate insertion. Obviously, a reusable capability is desirable.

Once a catheter is inserted into a vein, venipuncture is determined by the flow of blood into a portion of the needle. If a vein has been appropriately entered, the venous blood will readily flow into the needle in a substantial quantity. If a vein has not been appropriately punctured, as for example when the point of the needle is not disposed in the vein but rather in tissue surrounding the vein, there will not be substantial flow of blood into the needle, but rather only a scanty flow of blood.

To assist in the flow of blood from the vein into the needle, suction or low pressure apparatus may either be the result of the operator operating a plunger or piston outwardly to reduce the pressure within a syringe secured to the needle, or by piercing a membrane covering a low pressure tube, using a rubber covered, partially evacuated piston or syringe ampule into which the blood flows.

Two hands of an operator are required to insert the needle and catheter and to withdraw a sample of blood to insure venipuncture. Typically, a needle and catheter are inserted into a vein by an operator holding the catheter and needle in one hand, referred to as the first hand, and using the other hand, referred to as the second hand, to hold and palpate a vein. After locating the vein into which the catheter is to be inserted, the needle and catheter are slowly inserted by the first hand while the second hand remains holding the patient's arm or leg, thereby making certain that the vein is in proper alignment for the insertion. After venipuncture has been accomplished, two hands are still required to withdraw the blood from the vein in order to ascertain venipuncture. The operator releases hold of the patient's arm or leg by the second hand and grasps the syringe secured to the needle with the second hand, and then releases the hold on the syringe by the first hand. The first hand is then transferred to the piston or ampule of the syringe, while the second hand holds the syringe. The first hand then moves the ampule or piston to appropriately withdraw blood.

During the change of holds on the syringe, with the catheter insertion apparatus in the arm, and on the subsequent movement of the piston or ampule of the syringe, the needle may puncture a wall of the vein and thus prevent appropriate catheter insertion, even though proper venipuncture was originally accomplished. In a substantial number of cases, the puncturing of the vein is accomplished properly originally, and then in the withdrawal of blood operation to confirm the venipuncture, the venipuncture is lost or destroyed by piercing a wall of the vein.

The apparatus of the present invention comprises apparatus for inserting a catheter using a single hand to both insert the catheter and to withdraw the sample of blood. It accordingly overcomes the problem of the prior art which requires the changing of hands from the initial insertion of the apparatus to perform the function of withdrawing blood to confirm venipuncture.

U.S. Pat. No. 3,323,523 illustrated one type of catheter insertion apparatus in which capillary action only is used to assure venipuncture. The catheter is inserted into a vein using a cannula for the insertion and the catheter is disposed within the cannula. The cannula inserts includes a small diameter portion for ascertaining venipuncture which is vented to atmospheric pressure and accordingly fills with blood as a result of capillary action from the blood pressure of the patient. No separate pressurized compartment or other provision is used for collecting the venous blood. This is a relatively slow and unreliable method of confirming venipuncture, and this method is not widely used.

In U.S. Pat. No. 3,335,723, a catheter is inserted within a needle, with the needle as an external sleeve, with provisions for a flexible bulb flashback device connected to the catheter and needle. The flashback device is squeezed prior to insertion into the vein of a patient and is released to allow a supply of venous blood to flow into the needle to ascertain or confirm venipuncture.

U.S. Pat. No. 3,734,095 illustrates still a third type of catheter insertion apparatus which includes a needle disposed within a catheter and the needle is connected to a tab portion which is squeezed prior to and during venipuncture and released after venipuncture has been accomplished. The tab portion then includes a low pressure area which causes blood to be withdrawn from the vein into the tab.

The three types of apparatus typically require the use of both hands during the insertion and confirmation. A fourth style, and more used than the above three, is the typical apparatus described previously where the piston of a syringe is moved rearwardly to cause a low pressure area or partial vacuum in the syringe and into which area the blood flows. Again, as with the three patents described, two hands are required to operate the apparatus after venipuncture has been accomplished.

SUMMARY OF THE INVENTION

The apparatus described and claimed herein comprises apparatus for inserting a catheter into a vein and for withdrawing a portion of venous blood to confirm or ascertain venipuncture, and which requires the use of only one hand to insert the catheter and to withdraw blood.

Among the objects of the present invention are the following:

To provide new and useful apparatus for inserting a catheter into a vein;

To provide new and useful apparatus for confirming venipuncture after a catheter has been inserted into a vein;

To provide new and useful catheter insertion apparatus requiring only a single hand to use;

To provide new and useful apparatus for withdrawing blood from a vein;

To provide new and useful apparatus for inserting a catheter having reusable capacity in case of initial failure of venipuncture; and To provide new and useful catheter insertion apparatus that enables quick confirmation of a successful venipuncture.

BRIEF DESCRIPTION OF THE DRAWING

FIG. 12 is a perspective view of an alternate embodiment of the apparatus of the present invention.

FIG. 13 is a view in partial section of a portion of the apparatus of FIG. 12 taken generally along line 13—13 of FIG. 12.

FIG. 14 is a view in partial section of a portion of the apparatus of FIGS. 12 and 13 taken generally along line 14—14 of FIG. 12.

FIG. 15 is a view in partial section of an alternate embodiment of the apparatus of FIGS. 12-14.

FIG. 16 is a view in partial section of the apparatus of FIG. 15 taken generally along lines 16—16 of FIG. 15.

FIG. 17 is a view in partial section of the apparatus of FIG. 15 taken generally along line 17—17 of FIG. 15.

DESCRIPTION OF THE PREFERRED EMBODIMENT

Figure 1:
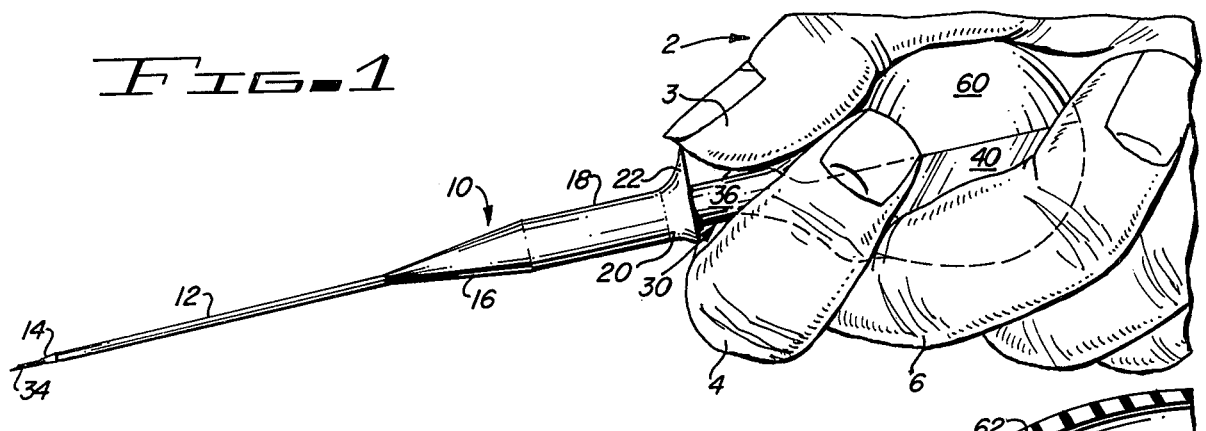
FIG. 1 is a perspective view of catheter insertion apparatus of the present invention shown held in the hand of a user.

FIG. 1 is a perspective view of a catheter 10 and a catheter insertion apparatus 30 shown as being grasped or held by a hand 2 of a user. The catheter 10 includes a relatively long but slender cannula 12 which includes a pointed front end or tip 14, both of which are inserted into a vein of a patient. Remote from the pointed end or tip 14 the cannula joins a conical portion 16 which flares outwardly and rearwardly from the cannula to a cylindrical connector or barrel portion 18. In use, fluid connectors or couplers connect to the catheter at the cylindrical portion 18 and may extend into the conical portion 16 to provide a fluid tight seal between the catheter 10 and a fluid delivery device or apparatus.

Flaring outwardly from the cylindrical portion 18 is a shield 20. The shield includes an upwarldy extending portion 22 which comprises a thumb rest against which a thumb 3 of the hand 2 is placed to disengage the insertion apparatus 30 from the cathether 10. In the alternative, or in addition, the thumb rest 22 is used to disengage and release fluid insertion apparatus from the catheter when the catheter is in use.

The insertion apparatus 30 includes a hollow needle which is disposed within the catheter and it includes a point 34 which is shown extending outwardly from the tip 14 of the cannula 12. The needle is secured to the insertion apparatus at a coupling portion 36, which in turn is secured to a pair of hollow members comprising a lower receptacle 40 and an upper vacuum member 60. In the illustration of FIG. 1, the hand 2 is grasping the apparatus, with the thumb 3 disposed adjacent the upwardly extending thumb rest 22 of the shield 20, and with the fingers of the hand extending underneath the apparatus such that the thumb and the fingers are used to grasp the apparatus. The thumb 3 is disposed on top of the upper member or vacuum bulb 60, while a forefinger 4 and a middle finger 6 are curled around the lower member or blood receptacle 40.

Figure 2:
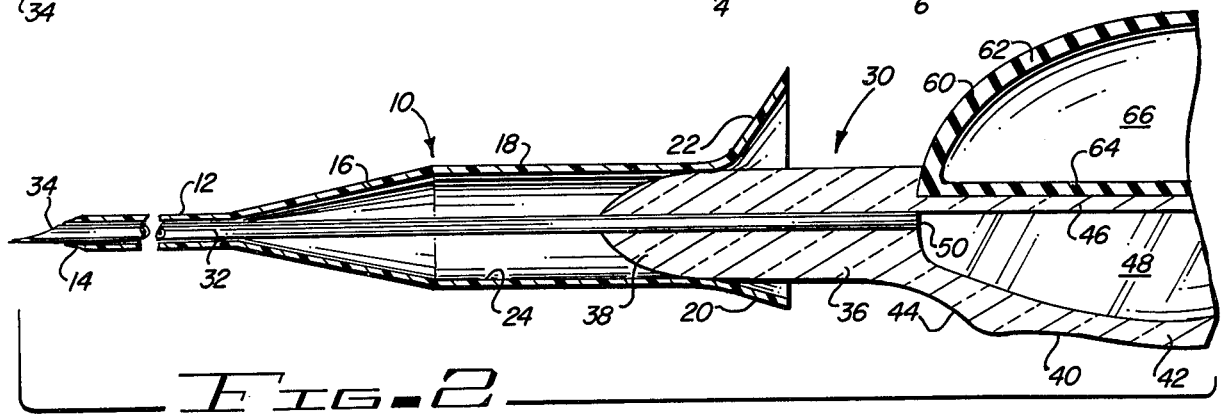
FIG. 2 is a view in partial section of a portion of the apparatus of FIG. 1.

FIG. 2 is a view in partial section of a portion of the apparatus of FIG. 1, showing the insertion apparatus 30 coupled together with the catheter 10. The insertion apparatus 30 includes a hollow needle 32, which is an elongated, hollow needle, relatively small in overall diameter and which includes a tapered point 34 designed to penetrate through the skin and into a vein, as is well known in the art. The metal needle 32 is secured to a coupling portion 36 of the insertion apparatus. The coupling portion and the blood receptacle or lower member 40 and the upper member or vacuum bulb 60 may be made of a plastic material, which are preferably either translucent or transparent.

The coupling portion 36 includes a convexly rounded nose portion 38. The coupling portion 36 is preferably cylindrical in configuration and the external diameter of the coupling portion is substantially equal to, or the same as, the interior diameter of the cylindrical barrel 18 of the catheter 10. The coupling portion 36, with its needle 32, is shown disposed within the cylindrical connector or barrel portion 18 of the catheter.

The needle 32 of the insertion apparatus is shown extending through the catheter, with the point 34 extending from the tip 14 of the cannula 12. It will be noted that preferably the interior diameter of the cannula 12 is slightly larger than the external diameter of the needle 32. From the cannula 12, the catheter increases in diameter in the conical or intermediate portion 16 to the cylindrical barrel portion 18, which is of a generally constant diameter.

At the proximal end of the catheter, remote from the cannula and its tip 14, is the flaring shield 20 with its upwardly extending thumb rest 22. The flaring shield 20 serves as a guide portion which receives the needle and nose portion 38 of the insertion apparatus 30. Obviously, care must be taken when inserting the needle 32 into the catheter to prevent the point 34 of the needle from scratching, or damaging or blunting itself or the catheter. When the catheter and insertion apparatus are ready for use, the nose 38 is disposed within a bore 24 of the cylindrical portion 18 of the catheter. The coupling portion 36 provides a seal to seal the bore 24 adjacent the flaring shield 20. Accordingly, the insertion apparatus in the catheter are secured together so that they act as a single unit during venipuncture. After venipuncture has been established, thumb pressure against the thumb rest 22 allows the insertion apparatus 30 to be withdrawn from the catheter and the catheter to be pushed forward into the vein. A coupling portion from, or associated with, a fluid delivery device is then inserted into the barrel 18 of the catheter, using the flaring portion 20 as a guide for inserting the fluid delivery apparatus.

Rearwardly of the coupling portion 36 is a lower member or blood receptacle 40. The blood receptacle includes a lower or bottom wall 42 and a depression 44 which serves as a finger rest during insertion of the catheter into a vein. Referring again to FIG. 1, the forefinger or index finger 4 is curled around the apparatus with the finger disposed in the finger rest or depression 44. The depression 44 is a convenience in the use of the apparatus, particularly in the withdrawal of the insertion apparatus 30 from the catheter. The lower or bottom wall 42 of the blood receptacle 40 is a continuation of the coupling portion 36 and is accordingly preferably molded of the same material. Again preferably, the blood receptacle 40 is relatively rigid, particularly as compared with the upper member or vacuum bulb 60. In general configuration, the bottom wall 42 is a somewhat flattened or dish shaped and elongated hemisphere. The receptacle 40 is closed by an upper or top wall 46, also preferably made of a relatively rigid plastic material. The lower or bottom wall and the top wall together define a chamber 48 into which blood flows from the interior of the hollow needle 32, through an orifice 50. The orifice 50 is the proximal end of the needle 32, and it communicates with, or opens into the chamber 48.

The upper member or vacuum bulb 60 includes a rounded, elongated, and inverted dish shaped top wall 62, and a bottom wall 64, which together define an interior chamber 66.

The bottom wall 64 of the upper chamber or vacuum bulb 60 and the upper or top wall 46 of the lower chamber or blood receptacle 40 are preferably both substantially planar and coextensive with each other. Moreover, they are disposed adjacent each other and are preferably secured together, as will be illustrated below and discussed in detail. The upper or tip wall 62 is preferably made of flexible material, such as rubber or a flexible or resilient plastic. The rigidity of the member 60 is substantially less than that of the receptacle 40, but yet is sufficiently rigid to allow for the insertion of the apparatus without unintentionally deforming during insertion, as illustrated in FIG. 1, when the thumb is disposed on top of the member 60. However, upon appropriate thumb pressure, the top wall 62 will flex sufficiently to allow air to be pumped out of the chamber 66, thus reducing the pressure within chambers 66 and 48, which in turn allows blood to be drawn into the lower chamber 48.

Figure 3:
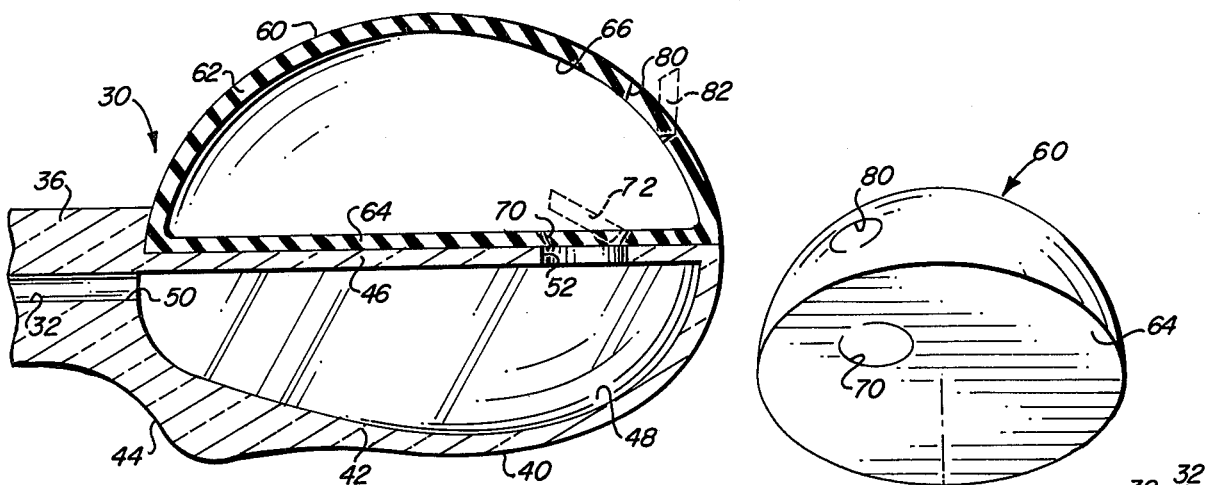
FIG. 3 is an enlarged view in partial section of a portion of the apparatus of FIG. 2.

FIG. 3 is a view in partial section of a portion of the apparatus of FIG. 2, comprising an enlarged view of the coupling portion 36 of the insertion apparatus 30 and the lower member 40 and upper member 60.

The lower member, or blood receptacle 40, is shown extending downwardly from the coupling 36 and is generally a continuation of the coupling portion. The wall 42 is a continuation of the coupling portion 36. Adjacent the juncture of the lower wall 42 and the coupling portion 36 is the finger rest or depression 44. The top wall 46 of the lower member 40 is generally flat or planar and is secured to both the coupling portion 36 and the lower or bottom wall 42. The wall 46 joins the coupling portion 36 above the orifice 56. The upper chamber or vacuum bulb 60 is disposed above, and substantially coextensive with, the lower member or blood receptacle 40, with the respective upper and lower walls of the two members disposed against each other.

The top wall 46 includes an aperture 52 extending through the wall. The aperture 52 is disposed beneath a tapering valve seat 70 which comprises an orifice or aperture extending through the bottom wall 64 of the vacuum bulb 60. The valve seat 70 tapers inwardly from the chamber 66 to the aperture 52. The valve seat receives a flapper valve 72 which is movably secured to the bottom wall 64.

At the rear or posterior end of the insertion apparatus 30 is another valve seat 80 extending through the top wall 62 of the upper member 60. The valve seat 80 tapers outwardly from the chamber 66 and its receives a flapper valve 82 which is movably secured to the top wall 62. While the flapper valve 72 moves within the chamer 66, the flapper 82 moves outwardly from the vacuum bulb or upper member 60. Both valves comprise one-way valves to draw air out of the chamber 48, into the chamber 66, and out of the chamber 66 to the ambient or outside air pressure. In turn, the lower pressure within the chamber 48 provides positive suction pressure to withdraw blood from a vein through the needle 32 and into the chamber 48 to confirm venipuncture.

Before the catheter insertion apparatus 30 and catheter 10 (see FIGS. 1 and 2) have been inserted into a vein, thumb pressure on the top wall 62 of the upper member or vacuum bulb 60 moves the relatively flexible top wall downwardly to compress chamber 66. The compression of the chamber results in a decrease in the total volume of the chamber and the decrease in volume is accompanied by a momentary increase in air pressure within the chamber 66 which causes the flapper valve 72 to close by being seated on its valve seat 70. At the same time, the increase in pressure within chamber 66 results in the opening of the flapper valve 82 away from its seat 80. With the opening of the valve 82, the pressure within the chamber 66 is reduced to atmospheric. As thumb pressure on the top wall 62 is released, the inherent flexibility of the wall 62 causes the wall to once again resume its normal shape or configuration. As the wall returns to its normal configuration, the chamber 66 enlarges to its normal size and the pressure within chamber 66 is reduced. This in turn causes the flapper valve 82 to close and the flapper valve 72 to open. The pressure within chamber 48 tends to equalize with respect to the pressure within chamber 66 through the valve 72 as the valve 72 moves off its seat 70. When the valve 72 is open, the aperture 52 and the aperture defined by the seat 70 comprise a conduit for the communication of pressure between the two chambers 48 and 66. As pressure within chamber 48 is reduced, there is a partial vacuum resulting within both chambers 48 and 66 which in turn causes the blood to be withdrawn through needle 32 into the chamber 48 through the orifice 50. The low pressure from chamber 48 is thus communicated by means of orifice 50 and needle 32 to the vein in which the apparatus is disposed. The combination of low pressure within chamber 48 and the blood pressure of the patient in whose vein the apparatus is disposed results in a confirmation or lack of confirmation of venipuncture in accordance with the flow of blood into the chamber 48.

Figure 4:
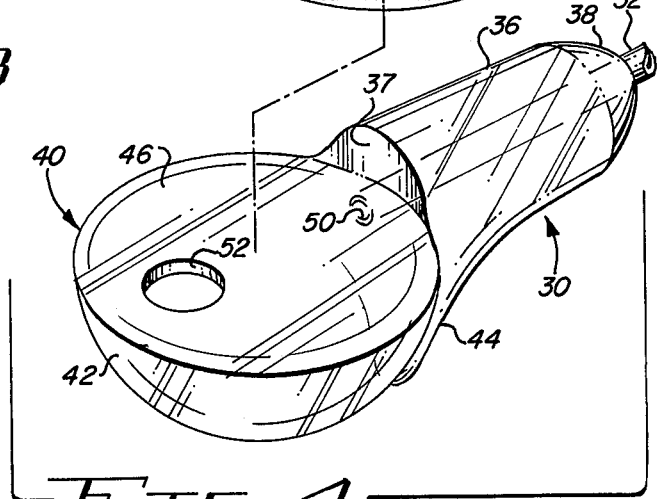
FIG. 4 is a perspective view, partially exploded, of a portion of the apparatus of FIGS. 1-3.

FIG. 4 is a perspective view of a portion of the apparatus of FIGS. 1-3 with the upper member or vacuum bulb 60 removed from the lower member 40 and the coupling portion 36 of the insertion apparatus 30. In FIG. 4, the insertion apparatus 30 appears to be transparent. If desired, it may be translucent. The reason for being either transparent or translucent, at least with respect to the lower member or blood receptacle 40, is to quickly and with certainty observe the blood flow from the needle 32 into the lower chamber 48 to confirm venipuncture.

The overall configuration of the blood receptacle 40 is clearly shown in the perspective view comprising FIG. 4. Preferably, the wall 42 is uniform in thickness except at the finger rest or depression 44. The lower member 40 is secured to, and may be part of, the coupling portion 36 of the insertion apparatus 30. The needle 32 extends rearwardly through the coupling portion and terminates at an orifice 50 at the chamber 48. Aperture 52 extends through the top wall 46, which is generally flat or planar in configuration. The top wall 46 mates with the bottom wall 64 of the top member or vacuum bulb 60.

Between the coupling portion 36 and the lower member 40 is a shoulder 37. The shoulder 37 extends upwardly from the top wall 46 and comprises a seat or stop against which the upper member 60 is disposed when the upper member 60 is assembled with, and accordingly secured to, the lower member 40.

The generally hemispherical configuration of the upper member 60 is also clearly shown in FIG. 4. The bottom wall 64 is generally flat or planar and is coextensive with the top wall 46 when the upper member 60 is secured to the lower member. The valve seat 70 defines an aperture which extends through the bottom wall 64 and is disposed substantially in contiguous relationship in the aperture 52 in the top wall 46 of the lower member 40. The two apertures accordingly comprise a conduit to provide communication between the lower chamber 48 and the upper chamber 66 of the lower and upper members, respectively.

Figure 5:
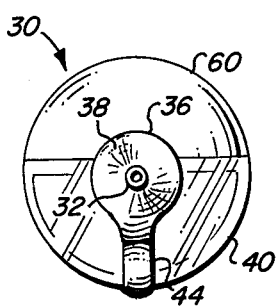
FIG. 5 is a front view of the catheter insertion apparatus of FIGS. 1-4.

FIG. 5 is a front view of the catheter insertion apparatus of FIGS. 1–4. From the front, the lower member 40 and the upper member 60 comprise a pair of generally hemispherical members which, when secured together as a working instrument, show from the front a generally circular configuration. Preferably, the lower and upper members may be somewhat elongated to provide for easier holding by an operator. The nose 38 is gently rounded, and of an elongated, convex configuration to seat and seal properly and appropriately within a catheter, as illustrated in FIGS. 1 and 2. The needle 32 extends outwardly from the nose 38 of the coupling portion 36 and comprises the instrument which punctures the skin and extends into a vein for the insertion of the catheter.

Beneath the coupling portion 36 and extending to the lower member 40 is the finger rest 44, against which a forefinger of a user (see FIG. 1) is disposed for ease in holding the apparatus and in withdrawing the catheter insertion apparatus 30 from the catheter, as illustrated in FIGS. 1 and 2.

The catheter insertion apparatus is relatively compact and is easily held and used by one hand of an operator, thus allowing the other hand of the operator to palpate and secure a vein for venipuncture. Moreover, the catheter insertion apparatus 30 may be used to confirm venipuncture by drawing blood into a chamber within the insertion apparatus without releasing hold of the catheter insertion apparatus with the other hand. That is, the hand used to grasp the catheter insertion apparatus and to insert the apparatus into a vein is also used to confirm venipuncture without releasing the initial hold on the apparatus and by merely applying thumb pressure on a portion of the insertion apparatus. The depression of the thumb in a pumping motion on the vacuum bulb portion of the catheter insertion apparatus results in a suction by means of low pressure within a blood receptacle chamber of the apparatus which provides positive pressure to draw blood through the needle of the catheter insertion apparatus into the chamber to confirm venipuncture. The apparatus accordingly is held in one hand during venipuncture, and the hold is not released during venipuncture. A separate squeeze action of the thumb of the user is used to confirm venipuncture without releasing hold of the apparatus. There is but a single insertion motion for both venipuncture and the confirmation of venipuncture using only one hand on the apparatus. This helps to prevent additional movements of the apparatus which could puncture the side walls of the vein in which the apparatus is inserted.

If desired, the apparatus may be inserted or rotated 180° to provide a reverse orientation of the insertion apparatus. The relatively rigid blood receptacle is then on top, with the user's thumb disposed thereon, while the index finger and middle finger of the user are disposed about the vacuum bulb. For confirmation of venipuncture, the index finger and middle finger apply pressure on the vacuum bulb, and the results are substantially as described above.

Flushing of the catheter insertion apparatus may easily be accomplished after failure of venipuncture by withdrawing the apparatus from the vein and by merely pumping the vacuum bulb. The apparatus provides a one way flow of a flushing agent in through the needle into the chamber 48, then into the chamber 66 and out of the apparatus through the orifice defined by the valve seat 80.

Figure 6:
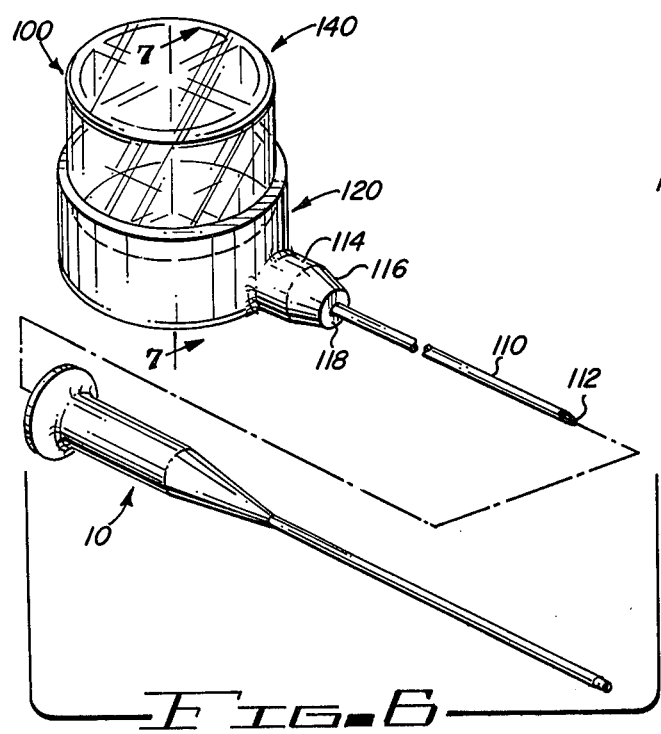
FIG. 6 is a perspective view, partially exploded, of an alternate embodiment of catheter insertion apparatus.

FIG. 6 is a perspective view of an alternate embodiment of the catheter insertion apparatus, disclosing a catheter 10, which is the catheter illustrated in FIGS. 1 and 2 above, with a compartmentalized vacuum packaged piston 140 disposed within a cylinder 120. The cylinder is connected to a needle 110. The needle 110 is substantially identical to the needle 32 of the embodiment of FIGS. 1-5. At the distal end of the needle is a point 112 which is cut at an oblique angle to the longitudinal axis of the needle 110. The needle obviously is a relatively long, slender, hollow metal tube, with a point designed to puncture through skin tissue and into a vein. The catheter 110 is disposed about the needle 110 during venipuncture, substantially identical to that shown in FIGS. 1 and 2, above. The catheter accordingly comprises, during venipuncture, an exterior sleeve about the needle 110.

The needle 110 is secured to a connector portion 114, which is a cylindrical protuberance extending outwardly from the lower portion of cylinder 120. The connector 114 includes an inwardly tapering conical nose portion 116 which comprises a guide portion for the insertion of the apparatus 100 into the catheter 10. The nose 16 may include a cutoff portion or shoulder 18 which is substantially perpendicular to the longidutinal axis of the needle 110 or it may include a continuation of the inwardly tapering nose portion 116, substantially as shown in FIGS. 2 and 4 with respect to the nose 38 of the catheter insertion apparatus 30.

Both the piston 140 and the cylinder 120 are preferably made of a clear or translucent polymerized material. There are numerous suitable plastics available out of which the apparatus may be made.

Figure 7:
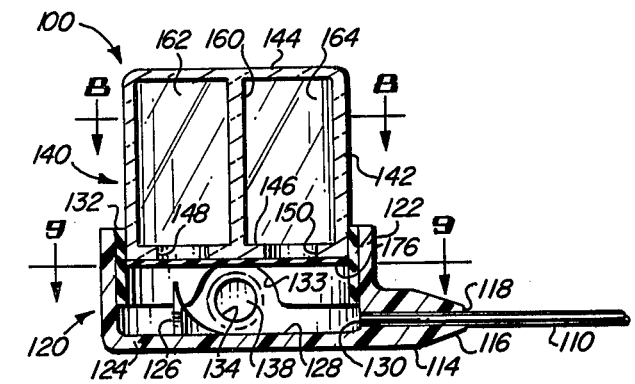
FIG. 7 is a view in partial section of the apparatus of FIG. 6 taken along line 7—7 of FIG. 6.

FIG. 7 is a view in partial section of the apparatus of FIG. 6 taken generally along line 7—7 of FIG. 6. It comprises a sectional view of the needle insertion apparatus 100 of FIG. 6. Cylinder 120 is shown, with connector portion 114 extending outwardly from the cylinder, and the needle 110 in turn extending outwardly from the connector 114.

Cylinder 120 comprises a relatively short cylinder having a wall 122 extending upwardly from, and secured to, a lower cylinder head or bottom 124. The connector 114 extends outwardly from a portion of the cylinder wall 122 adjacent the lower head 124. Disposed within the cylinder 120, and extending upwardly from, and secured to, the lower head 124 is a curved knife blade 126. The knife blade 126 is located in substantial alignment with an orifice 130 which comprises the juncture of the needle 110 with the interior of the cylinder wall 122. The orifice empties into a chamber 128 defined by the interior of the cylinder walls 122 and the interior of the lower cylinder head 124.

The knife blade 126 is in line with needle 110 but is not disposed in the center of the cylinder 120. Rather, it is disposed off-center slightly so as to be aligned with compartments within piston 140, as discussed below.

Piston 140 includes a cylindrical wall 142 closed at its top or upper portion by an upper or top piston head 144 and by a bottom or lower piston head 146. A pair of apertures 148 and 150 are shown extending through the bottom head 146. A central wall 160 extends between the top and bottom heads 144 and 146, respectively. The wall 160, with another central wall 170 (see FIG. 8), both of which are disposed substantially perpendicular to each other and extend between the top head 144 and bottom head 146 and diametrically across the cylinder from one side of the wall 142 to the opposite side, divide the cylinder 140 into four separate compartments, of which compartments 162 and 164 are shown in FIG. 7.

The compartments within the piston 140 are sealed by a diaphragm or membrane 176 which is sealingly secured to the bottom head or wall 146. The diaphragm or membrane 176 may be made of a material such as rubber, or of an elastomeric or plastic material which may be punctured by the knife 126 when downward pressure is placed on the piston 140 to provide relative motion between the cylinder 120 and the piston 140. The aperture 148 is shown in FIG. 7 aligned with the knife blade 126. Accordingly, when appropriate pressure is placed on both the cylinder and the piston to provide downward movement of the piston with respect to the cylinder and the knife blade, the knife blade will cut the membrane 176 at the location of the aperture 148.

The compartmentalized piston 140 is sealed with the membrane or diaphragm 176 after the compartments within the piston have been at least partially evacuated of atmospheric pressure to provide a low pressure or partial vacuum within each of the compartments. Accordingly, when the knife 126 cuts or ruptures the membrane 176 in the area of an aperture, the compartment communicates directly with the chamber 128 of the cylinder beneath the compartment to subject the chamber 128 to the low pressure within the compartment of the piston. In this manner, the chamber 128 beneath the piston and within the cylinder 120 is subject to a partial vacuum or low pressure which results in the needle 110 also being subject to the low pressure. In turn the low pressure developed results in a suction force applied through the needle 110 to assist in drawing blood from a vein through the needle 110 and into the chamber 128.

The piston 140 and the cylinder 120 are movably sealed by an interior seal or gasket 132 which is disposed on the inner periphery of the cylinder wall 122. The exterior of the cylindrical wall 142 of the piston 140 is in direct contact with the seal 132 to insure that atmospheric pressure from the ambient air outside the piston and cylinder does not leak into the chamber 128 to compensate for the lower pressure or partial vacuum within a compartment as the membrane 176 is pierced by the knife blade 126. If desired, an appropriate seal or gasket may be disposed on the outside of the piston rather than on the inside of the cylinder. For example, the diaphragm or membrane 180 may be curled or curved about the outside of the cylindrical wall 142 and extend upwardly along the wall 142 to provide a seal, or to comprise a gasket to seal the cylinder and the piston.

As stated above, venipuncture is accomplished in only about fifty percent of the attempts. Accordingly, if venipuncture is not accomplished and the lack of blood flowing into the chamber 120 through the orifice 130 from the needle 110 confirms a failure of venipuncture, the cylinder 140 may be lifted or raised relative to the knife 126 and accordingly upwardly relative to the cylinder 120 and the piston 140 may then be rotated to align another compartment over the knife blade 126. For example, in FIG. 7 the compartment 162 is shown aligned over the knife 126, with the portion of the diaphragm 180 beneath the aperture 148 subject to the knife 126. If venipuncture is not accomplished, the piston may then be rotated to align compartment 164 and aperture 150 with the knife 126. The catheter insertion apparatus 100 may then be used to again attempt to insert a catheter into the desired vein.

For flushing purposes, the cylinder 120 may include an aperture 134 closed by a one way valve 138. The aperture 134 extends through the cylinder wall 122. The orifice and valve are used to flush the cylinder of any blood from an initial, and failed, attempt at venipuncture. The cleaning or flushing of the cylinder may be accomplished after the needle and catheter are withdrawn from the vein, and prior to rotation of the piston by the pumping action of raising and lowering the piston 140 relative to the cylinder 120 to cause an inflow of a flushing agent into chamber 128 through the needle 110 and out of the chamber 110 through the aperture 134.

Figure 8:
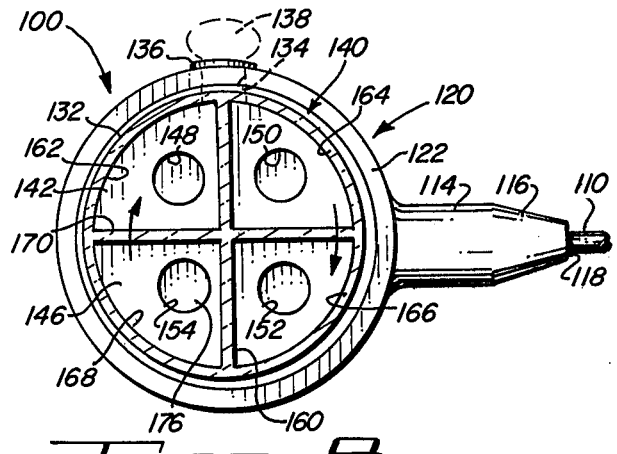
FIG. 8 is a view in partial section of a portion of the apparatus of FIG. 7 taken generally along line 8—8 of FIG. 7.

FIG. 8 is a view of the apparatus of FIG. 7 taken generally along line 8—8 of FIG. 7, and comprises a sectional view looking downwardly through the piston 140 and at the cylinder 120. The connector portion 114, with its nose 116 is shown with the needle 110 extending outwardly therefrom. The shoulder 118 at the juncture of the needle 110 and the nose 116 is also clearly shown. The connector portion 114 extends radially outwardly from the cylinder 120.

Disposed within the cylinder 120, and secured to the inner periphery of the cylinder wall 122 is the seal 132. The exterior periphery of the cylindrical wall 142 of the piston 140 is in direct contact with the seal 132. The aperture 134 is shown extending through the wall 122 of the cylinder and is shown in phantom. A boss 136 is disposed circumferentially about the aperture 134 on the outer periphery of the wall 122. The boss provides a relatively flat surface and it includes a seat for the valve 138, which is shown in phantom in an open position in FIG. 8.

With respect to the piston 140, one of its interior walls 160 is shown extending diametrically across the piston and aligned with the aperture 134. The piston also includes another central wall 170 also extending diametrically across the piston at substantially a right angle to the wall 160. Both interior walls 160 and 170 are sealingly secured to, and are a part of, the interior of the piston. As shown in FIG. 8, the interior walls divide the piston into four compartments, compartments 162, 164, 166, and 168. The top of each compartment is closed by the top cylinder head 144, (see FIG. 7) and by the bottom cylinder head 146 (also shown in FIG. 7.) Extending through the bottom head 146 in each of the respective compartments is a plurality of apertures 148, 150, 152, and 154. The apertures, and accordingly the compartments, are sealed by the diaphragm or membrane 176, which is sealingly secured to the bottom head 146.

Directional arrows are shown in FIG. 8 extending across the interior wall 170 to indicate that the piston 140 may be rotated within the cylinder 120.

Figure 9:
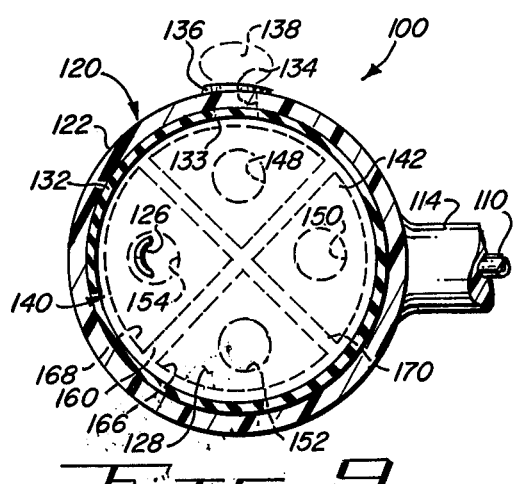
FIG. 9 is a view in partial section of a portion of the apparatus of FIG. 7 taken generally along line 9—9 of FIG. 7.

FIG. 9 is a view of the apparatus of FIG. 7 taken generally along line 9—9 of FIG. 7, showing the lower portion of the cylinder 120 with the piston 140 rotated in the direction indicated in FIG. 8 by the arrows to align aperture 154 of compartment 168 with the knife blade 126. As shown in FIG. 9, the catheter insertion apparatus 100 is in a use position and accordingly downward pressure on the piston 140 with upward pressure on cylinder 120 to provide downward relative motion or movement between the piston and the cylinder will result in knife blade 126 contacting and piercing the diaphragm or membrane 176 (see FIGS. 7 and 8) to subject the chamber 128 (see FIG. 7) beneath the piston 140 to the low pressure or partial vacuum of the compartment 168. In turn, this will result in blood being drawn through the needle 110 into the chamber 128 if venipuncture has been accomplished. It will be noted that the piston 140, with its wall 142 and interior walls 160 and 170, and the apertures 148, 150, 152, and 154 are shown in phantom for illustrative purposes, while the chamber 128 is generally designated as the interior of the cylinder 120. The interior peripheral seal or gasket 132 is shown on the interior of the cylinder wall 122. The cutout or relieved portion 133 of the seal 132 is shown disposed about the aperture 134 at the juncture of the aperture 134 and the cylinder wall 132. The boss 136 and the valve 138 are also illustrated in FIG. 9, with the valve 138 in the open position as also shown in FIG. 9.

Figure 10:
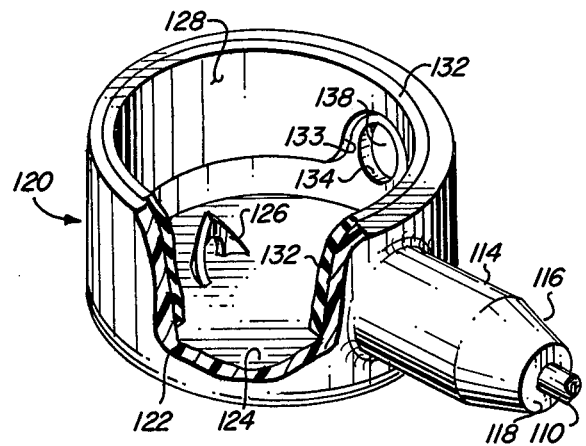
FIG. 10 is a perspective view of a portion of the apparatus of FIGS. 6-9.

FIG. 10 is a perspective view of the cylinder 120, with a portion of the cylinder wall 122 and the seal 132 cut away to show the interior of the cylinder.

The seal 132 is secured to the inner periphery of the cylinder wall 122. The seal 132 includes a relieved portion 133 disposed about the drain or flushing aperture 134. The aperture 134 is closed by a valve 138 which is a one-way check valve allowing only a flow out of the chamber 128 of the cylinder 120.

The knife 126 is shown extending upwardly from the bottom head or wall 124 of the cylinder 120. The knife 126 is aligned diametrically with the needle 110, which is shown extending out of, and secured to, the connector 114.

The nose portion 116 of the connector 114 is, with respect to the shoulder 118 and the connector 114, an inwardly extending truncated conical portion. It tapers inwardly from the cylindrical connector 114 to the shoulder 118 and, as discussed above, makes contact with the interior of the catheter 10, shown in FIG. 6.

Figure 11:
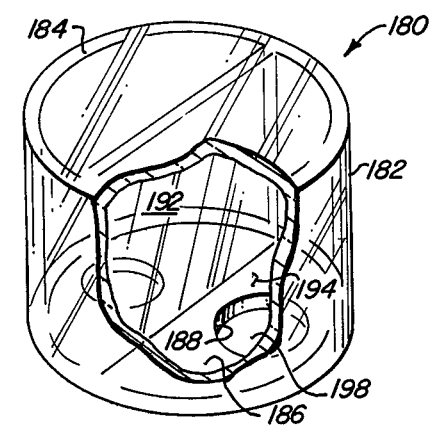
FIG. 11 is a perspective view with a portion cut away of an alternate embodiment of a portion of the apparatus of FIGS. 6-9.

FIG. 11 is a perspective view with a portion cut away of an alternate embodiment of cylinder 140, comprising a cylinder 180. The cylinder 180 is a two-compartment cylinder, rather than a four-compartment cylinder, such as cylinder 140 of FIGS. 6–9.

The cylinder 180 includes a cylinder wall 182 and a top wall or cylinder head 184 which closes the top of the cylinder. A bottom cylinder head or cylinder wall 186 closes the bottom of the cylinder. A wall 192 extends diametrically across the cylinder 180 to divide the interior of the cylinder into a pair of compartments, including a compartment 194. The interior wall 192 is secured to the inner periphery of the cylinder wall 182 at diametrically opposite locations and it extends axially the entire length of the cylinder between the top cylinder head 184 and the bottom cylinder head 186, both of which it is sealingly secured to. The bottom cylinder head 186 includes a pair of apertures extending through the cylinder head and located respectively in each compartment. An aperture 188 extends through the lower cylinder head 186 and communicates with the compartment 194. A diaphragm or membrane 198 is sealingly secured to the exterior of the bottom cylinder head 186 to close the apertures.

When the piston 180 is disposed in an appropriate cylinder, such as cylinder 120, the chamber 194 may be appropriately positioned so that the knife 126 is adjacent the aperture 188. Relative motion between the cylinder and the piston, with the piston moving into the cylinder, will result in the knife 126 piercing through the membrane or diaphragm 198 to thus allow the chamber 128 beneath the piston 120 to communicate with the interior of the compartment 194. With a partial vacuum sealed into the compartment 194, the communication between the chamber 128 and the compartment or chamber 194 will thus result in pressure within the chamber 128 at less than atmospheric pressure to help draw blood from the vein through the needle 110 and into the chamber 128 to confirm venipuncture. In the alternative, a lack of blood or a minimum of blood will confirm that venipuncture has not been accomplished.

FIG. 12 is a perspective view of an alternate embodiment of catheter insertion apparatus of the present invention, comprising an elongated cylindrical catheter insertion apparatus 200. The apparatus 200 includes an elongated, slender hollow metal needle 210 extending axially outwardly from the apparatus from a tapered nose 210 which extends outwardly from a cylindrical portion 212. The cylindrical portion 212 is a front cylindrical portion which is spaced apart from a rear cylindrical portion 280. Between the front and rear cylindrical portions 212 and 280 is a center cylindrical portion 240. The cylindrical portion are hollow and are appropriately valved to provide for the inflow of blood through the needle 210 and for the outflow of air from the interior of the apparatus to provide for a partial vacuum or low pressure within the apparatus to aid in the withdrawal of blood from a vein in which the needle is inserted into the apparatus.

FIG. 13 is a view of the apparatus of FIG. 12 taken generally along line 13—13 of FIG. 12, and comprising a view in partial section of the catheter insertion apparatus 200. Within the front cylindrical portion 212 is a bore 216. The bore 216 includes an inwardly tapering portion 215. The inwardly tapering bore 215 extends coaxially forward of the bore 216 into the nose portion 214. Within the bores 215 and 216 is a chamber 226. The needle 210 communicates with the bore 215, and accordingly with the bore 216, by means of an orifice at the juncture of the needle 210 and the bore 215. Flow through the orifice is permitted only from the needle into the chamber 226 by a one-way valve 218 which is disposed at the front end of the bore 215 adjacent the needle 210. The valve 218 includes its own seat disposed on a forward shoulder of the bore 215 within the nose 214. The valve 218 opens into the bore 215 to allow for the inflow of blood from the needle 210, but closes to prevent the outflow of blood when the pressure increases within the bores 215 and 216. At the end of the bore 216 remote from the bore 215 is a radially inwardly extending flange 220. A shoulder 222 is formed on the outer periphery of the forward cylindrical portion 212 adjacent to, but forward of, the radially extending flange 220. Between the shoulder 222 and the flange 220 is a reduced diameter portion 224. The inwardly extending flange 220 is connected to, or extends from, the reduced diameter cylindrical portion 224 remote from the shoulder 222.

An inner slotted cylinder 230 extends axially rearwardly from the front cylindrical portion 212 from the flange 220, to which it is appropriately sealingly secured. The slotted cylinder 230 includes a pair of open ends 232 and 234, spaced apart from each other. The forward or front end 232 is open to, and accordingly communicates directly with, the bore 216.

The slotted cylinder 230 includes a plurality of axially extending slots 236 spaced apart from a plurality of axially extending ribs 238. The ribs 238 comprise the "walls" of the slotted cylinder 230. The ribs are preferably slightly wider than the width of the slots.

Within the cylinder 230 is a chamber 244 which communicates with chamber 226 through the open end 232. The cylinder 230 includes a radially outwardly extending flange 240 which is secured to the end 234 of the cylinder. A rear cylinder wall 250 extends axially rearwardly from the flange 240. The cylindrical portion or cylinder wall 250 includes a reduced diameter portion 252 disposed between the flange 240 and a shoulder 254. The external diameter of the reduced portion 252 is substantially the same as the external diameter of the reduced diameter portion 224 of the cylindrical portion 212. The external diameter of the cylinder wall 250 is substantially the same as the external diameter of the forward or front cylindrical portion 212. The cylindrical portions 212 and 250 are axially aligned and their outer peripheries are accordingly matching.

The cylinder 250 also includes an inner reduced diameter portion 256 extending axially rearwardly from an inner shoulder 258. The cylinder 250 is closed by an end cap 270. The end cap 270 includes an axially extending flange 272 which seats against the shoulder 258 on or in the reduced diameter portion 256 of the cylinder 250. A chamber 260 is defined by the cylinder 250, end cap 270, and the end 234 of the inner cylinder 230. The chamber 260 communicates with chambers 226 and 244 through the open end of the cylinder 230.

The end cap 270 includes a one-way valve 274 which moves to open or close an aperture 276 extending through the end cap 270. The aperture 276 also includes an appropriate seat for the valve 274.

The slotted cylinder 230 is secured to the flange 220 of the forward or front cylindrical portion 212, and the end cap 270 is sealingly secured to the inner reduced diameter portion 252 of the cylinder 250, to provide a unitary elongated cylinder of a substantially constant or uniform outer diameter, except for the central portion, exteriorally of the slotted cylinder 230. The central portion of the apparatus, exteriorally of the slotted cylinder 230, is covered by a flexible or deformable sleeve 280. The deformable sleeve 280 is secured against the shoulders 222 and 254 at the reduced diameter portions 224 and 252. The exterior diameter of the sleeve 280 in its normal or rest position is substantially the same as the front cylindrical portion 212 and the rear cylindrical portion 250 so that a uniform exterior is achieved with the apparatus in the normal, rest position.

Between the sleeve 280 and the cylinder 230 is a variable sized chamber 246. The chamber 246 may also be referred to as a pumping chamber because deformation or squeezing of the sleeve 280 results in a pumping action as described below. The ribs 238 limit the inward deflection or deformation of the sleeve and accordingly the ribs control the pumping action of the apparatus. With only a limited inward deflection of the sleeve 280 on each inward pumping stroke, there is less liklihood of an undesirable and uncontrolled movement of the apparatus after insertion of the catheter which could result in a puncture of a venous wall by the needle 210.

The chambers 226, 244, and 260 together comprise an elongated chamber which communicates with pumping chamber 246 through the slots 236. Flow into and out of the chamber 226-244-260 is controlled by the valves 218 and 274 in response to movement of the sleeve 280 and pumping chamber 246.

In use, the needle 210 and nose 214 are inserted into a catheter, such as illustrated above in conjunction with FIGS. 1, 2, and 6, and the needle 210 is used to pierce the skin and a vein to insert a catheter into the vein. The apparatus 200 is relatively slim and elongated so as to enable the user to easily grasp the apparatus with a thumb and opposing fingers and thus enable the apparatus to be disposed in a relatively low profile or low angle with respect to the skin on the limb or body member on which venipuncture is to be accomplished. After the needle 210, with its catheter, has been inserted into a vein, the user simply applies an inward pressure or opposing pressure on the sleeve 280 with thumb and fingers to deform the sleeve inwardly against the ribs 238, as shown in phantom in FIG. 13. The ribs 238 act as a stop to limit the inward movement of the sleeve and to strengthen and stiffen the entire apparatus. When the inwardly directed pressure is released, the sleeve 280 returns to its normal, rest position, as shown in FIG. 13. The inward and outward movements of the sleeve comprise pumping strokes to pump air out of the chambers of the apparatus and to pump blood through needle 210 into the apparatus.

During the inward movement of the sleeve 280, the valve 218 closes to prevent a flow of pressure from within the apparatus from escaping or moving into the needle 210, and at the same time the valve 274 opens to allow the pressure to flow outwardly from the cylindrical apparatus. The closing of valve 218 and the opening of valve 274 is in response to a momentary increase in the pressure due to the deformation of the sleeve and the accompanying decrease in the internal pressure within the cylinder. As the pressure is released on the sleeve and the sleeve returns to its normal configuration, the valve 274 closes and the valve 218 opens.

As the valve 274 opens, the pressure within the chamber equalizes with the outside ambient atmospheric pressure, and when the sleeve 280 returns to its normal position, a low pressure or partial vacuum within the chamber results. The reduced pressure caused by the expansion of the chamber to its normal size, which accompanies the return of the sleeve 280 to its normal size, results in the closing of the valve 274 and the opening of the valve 218. With the needle 210 subject to the low pressure or partial vacuum from within the chamber(s) inside the cylinder, the flow of blood through the needle 210 into the chamber(s) is assisted to confirm venipuncture, or, in the alternative, to confirm that venipuncture has not been accomplished.

FIG. 14 is a view in partial section of the apparatus of FIG. 13, taken generally along line 14—14 of FIG. 13. The figure comprises a sectional view of the apparatus looking towards end cap 270. Valve 274 is axially centered in the end cap 270.

The sleeve 280 is shown disposed about the slotted cylinder 230, and spaced apart from the ribs 238. The slotted cylinder 230 includes a plurality of slots 236 between the ribs 238. The area between the sleeve 280 and the inner cylinder 230 comprises the pumping chamber 246, which communicates with the inner chamber 244 through the slots 236.

Due to the symmetrical configuration of the apparatus 200, a particular orientation of the apparatus is unnecessary in accomplishing the insertion of the catheter. The catheter insertion apparatus 200 may accordingly be used with a catheter by grasping or holding the apparatus in any convenient manner by the user. For the pumping action to evacuate air disposed within the apparatus to aid in the withdrawal of blood from a vein into the apparatus to confirm venipuncture, preferably thumb and finger pressure, oppositely directed, is used. The user simply applies a squeezing force to the sleeve 280 to deform the sleeve against the ribs 238. By squeezing the sleeve against the ribs, the chamber 246 is reduced in size, thus momentarily increasing the pressure within the chamber 246 and the chamber 244, and also the chambers 226 and 260 (see FIG. 13). The momentary increase in the pressure of the chambers results in a closing of the valve 218 (see FIG. 13) as discussed above, and an opening of the valve 274 to relieve the pressure by venting the apparatus 200 to ambient atmospheric pressure outside the apparatus. When the squeezing pressure is released, the sleeve 280 returns to its normal, circular cylindrical configuration, as indicated in FIGS. 12, 13, and 14, which results in an increase in the size of the chamber 246 and accordingly of a decrease in the pressure of the large chambers 226-244-260, and an accompanying closing of valve 274 and opening of valve 218 (see FIG. 13). Blood is then drawn into the apparatus through the needle 210, as discussed above.

For convenience, the entire apparatus, including the sleeve 240, may be made of appropriate clear or translucent materials. If desired, the sleeve 280 may be made of rubber or of a plastic having the appropriate properties. The balance of the apparatus may also preferably be made of an appropriate plastic.

Both FIGS. 13 and 14 illustrate the concentric relationship between the movable or pumping chamber 246 and the fixed, combination chamber 226-244-260. If the chambers 244 and 260 are considered as part of the movable or pumping chamber 246, due to the presence of valve 274 which opens in response to deformation of sleeve 280, then there is both a concentric and coaxial relationship between the fixed chamber 226 and the movable chamber.

FIG. 15 is a sectional view of an alternate embodiment of the catheter insertion apparatus of FIGS. 12–14. It is a generally cylindrical, in-line type of insertion apparatus, such as disclosed in FIGS. 12–14, but it differs in that the pumping arrangement is somewhat different. Catheter insertion apparatus 300, as illustrated in FIG. 15, includes a needle 310 extending axially forward from a conical nose 314, which comprises a forward cylindrical portion 312, and which is substantially identical to the embodiment illustrated in FIG. 13. As in the prior embodiments, the conical or forwardly and inwardly tapering nose 314 allows the apparatus to be guided and inserted appropriately into a catheter.

Within the cylindrical portion 312 is a bore 320, closed at its forward or front end by an end wall 322. The needle 310 communicates with the bore 320 through the end wall 322. The end wall 322 includes a one-way valve, 324, which allows only an inflow from the needle 310 into a chamber 326 defined within the bore. The valve 324 closes to prevent an outflow from the chamber 326 into the needle 310. The needle 310 communicates with the chamber 326 through an orifice at the end wall 322 and within a valve seat on the end wall for the valve 324.

The cylinder 312 includes an exterior radially extending shoulder 330 which extends from the exterior periphery of the cylinder 312 to a reduced diameter portion 332. The reduced diameter portion 322 terminates at an end 334 of the cylinder 312 remote from the nose 314.

Adjacent the end 334 of the cylinder 312, and within the bore 320, is disposed an inner slotted cylinder 340. The inner slotted cylinder 340 includes a forward end 342 which is disposed in, and sealingly secured to, the bore 320 forwardly of the end 334. The end 342 of the cylinder 340 is open and communicates directly with an interior bore 346 within the slotted cylinder 340. The slotted cylinder 340 includes a rear end 344 remote from the forward end 342, and the rear end 344 is also open, the same as the forward end 342.

The inner slotted cylinder 340 includes a plurality of slots 348 which extend axially along the cylinder. A plurality of axially extending ribs 350 are spaced apart to define the slots 348. Within the cylinder 340 is a chamber 352. The chamber 352 comprises a continuation of the chamber 326 and the flow therebetween is generally unrestricted.

A sleeve 360 is disposed about, and spaced apart from, the slotted cylinder 340. The sleeve is secured to the front cylinder 312 at the shoulder 330 and the reduced diameter portion 332. The sleeve 360 comprises an elongaged cylinder 362 which includes an open end 364 seated against the shoulder 330 of the front cylinder 312. The rear end of the cylinder 362 is closed by an end wall 366. The closed end wall includes an aperture or valve seat 368 which receives a one-way valve 370. The valve 370 controls the flow through the aperture or valve seat and allows only an outflow from within the sleeve.

Externally of the slotted cylinder 340 and within the sleeve 360 is a pumping chamber 372. The pumping chamber 372 is a variable size chamber, the size of which decreases when an inwardly directed force is applied on the cylinder 362, moving the sleeve, or portions of the sleeve, toward the slotted cylinder 340, the ribs 350 of which limit the inward deformation of the sleeve. When the squeezing force is released, the chamber expands to its normal size, as shown in FIG. 15. The user of the apparatus accordingly applies a squeezing force to squeeze the sleeve 360 against the ribs 350 of the slotted cylinder to cause an outflow through the valve 370 resulting from a momentary increase of the pressure within the chambers 326, 352, and 372. The increase in pressure also results in the closing of the valve 324.

The open end 344 of the slotted sleeve 340, with the slots 348, allow for a substantially unrestricted communication among the respective chambers in the catheter insertion apparatus 300. The inwardly directed force, or squeezing action, by the user of the apparatus 300 decreases the size of the chamber 372 with a resulting increase in the pressure within the chamber closing valve 324 and opening valve 370. When the pressure is released, the expansion of the chamber 372 to its normal size reduces the pressure within the chambers, thus closing the valve 370 and opening the valve 324. The low pressure or partial vacuum within the apparatus thus assists in the flow of blood through the needle 310 and into the chamber 326 - 352 - 372 to confirm venipuncture, or in the absence of such flow of blood, to confirm that venipuncture has not been accomplished. The apparatus 300, including the cylinders 312 and 340, and also the sleeve 360, are preferably made of clear or translucent material, such as plastic, so that the flow of blood into the apparatus through the needle 310 may easily be observed visually. As discussed above in conjunction with the embodiments of FIGS. 12-14, the sleeve 360 may be fabricated of either a plastic or a rubber, as appropriate and as desirable. If required, the closed end 366 of the sleeve 360 may be thicker than the cylindrical portion 362 so as to preclude deformation of the aperture 368 when the pumping action, the squeezing of the sleeve, is accomplished by the user. Obviously, if the aperture or valve seat 368 is deformed, the valve 370 may not function as desired.

The pumping or movable chamber 372 is disposed partially coaxially and partially concentrically with respect to the fixed chamber 326 and to the chamber 352.

FIG. 16 is a view in partial section of the apparatus of FIG. 15 taken generally along line 16—16 of FIG. 15. It comprises a view looking toward the rear end 366 of the apparatus 300 along the longitudinal axis of the apparatus. The pumping chamber 372 is shown between the flexible cylindrical portion 362 of the sleeve 360 and the inner slotted cylinder 340. Communication between a chamber 372 and the chamber 352 within the slotted cylinder 340 is provided by the slots 348, disposed between the ribs 350.

The valve 370 is concentrically located with respect to the rear end wall 366. The valve 370 opens and closes in accordance with pressure changes within the apparatus 300 to provide for a one-way flow, an outward flow, from the apparatus. The valve 370 is accordingly a one-way valve.

FIG. 17 is a view of the apparatus of FIG. 15, taken generally along line 17—17 of FIG. 15. It comprises a view in partial section through the apparatus 300, looking toward the front of the apparatus. The sleeve 360 is shown disposed concentrically about the inner slotted cylinder 340, and the cylindrical portion 362 of the sleeve 360 is secured to the forward cylindrical portion 312 of the apparatus 300 at and about the open end 334 of the front cylindrical portion 312. The slotted cylinder 340 is also secured to the front cylindrical portion 312 (see FIG. 15) at the end 334.

The valve 324 is disposed in the front end wall 322 and controls the flow of fluid (or air) from the needle 310 (see FIG. 15) into the chamber 326. The valve 324 is a one-way valve allowing for the inflow of fluid (air, blood, or whatever) from the needle 310 into the chamber 326. The chamber 326 communicates with the chamber 352 (see FIGS. 15 and 16) which is disposed within the slotted cylinder 340, and in turn communication between the chamber 352 and the chamber 372 is provided by the plurality of slots 348 between the ribs 350 of the slotted cylinder 340.

The embodiments of FIG. 12-14 and of FIGS. 15-17 are similar, and work on a common principal, differing only in the structure of the respective sleeves and pumping chambers within the sleeves. Both embodiments provide for an in-line type catheter insertion apparatus which, under some circumstances, may be easier to use than the catheter insertion apparatus disclosed above in conjunction with FIGS. 1-11. However, all of the catheter insertion apparatus disclosed herein allow for the insertion of a catheter and the confirmation of venipuncture using only a single hand to insert the catheter into a vein and to confirm venipuncture with the same hand without relaxing the initial hold or grasp of the user's hand on the catheter insertion apparatus. This allows the user's other hand to maintain a hold on the limb in which venipuncture and catheter insertion is to be accomplished.

A simple squeezing action is used with all apparatus disclosed herein by applying an oppositely directed pressure or force between the user's thumb and fingers to cause a low pressure or partial vacuum within the apparatus to assist in drawing venous blood through the needle of the catheter insertion apparatus and into a chamber within the apparatus to confirm that venipuncture has or or has not been accomplished. Moreover, each of the apparatus may easily be flushed if venipuncture has been unsuccessful in the first instance, and may be used in a subsequent attempt at venipuncture to accomplish the insertion of a catheter into a vein.

It will be noted that in each of the embodiments pressure is applied in a direction substantially perpendicular to the longitudinal axis of the needle to provide the low pressure or partial vacuum in a chamber to draw blood through the needle and into the chamber to confirm that venipuncture has or has not been accomplished. The pressure may be applied without releasing the hand hold on the apparatus by which insertion of the apparatus, together with a catheter, into a vein is originally accomplished.

In each case, there are a pair of chambers defined within the apparatus, one, a blood receiving chamber into which the blood flows directly from the needle and accordingly which communicates directly with the needle, and another chamber which is sometimes referred to as a pumping chamber, and which communicates with the blood receiving chamber, to provide low pressure or a partial vacuum in the blood receiving chamber.

What is claimed is:

1. Catheter insertion apparatus comprising, in combination:
    an elongated hollow needle for insertion into a catheter and, with the catheter, into a vein;
    a nose portion adjacent the needle for insertion into a catheter and against a flaring portion of the catheter;
    chamber means, including
        a first chamber adjacent the nose portion and communicating with the needle to receive a flow of blood from the needle;
        a second chamber adjacent to and communicating with the first chamber and movable relative to the first chamber to provide a partial vacuum in the first chamber to enhance the flow of blood through the needle into the first chamber; and
        valve means located in said chamber means for providing a one-way flow of blood into the first chamber and a one-way flow of air out of the second chamber.

2. The apparatus of claim 1 in which the second chamber moves relative to the first chamber in a direction substantially perpendicular to the longitudinal axis of the needle.

3. The apparatus of claim 2 in which the first and second chambers comprise a pair of generally hemispherical chambers disposed contiguously adjacent each other.

4. The apparatus of claim 2 in which the second chamber is concentrically disposed with respect to the first chamber.

5. The apparatus of claim 4 in which the first chamber includes a cylinder having a plurality of spaced apart ribs extending generally axially with respect to the needle for limiting the deformation of the second chamber.

6. The apparatus of claim 5 in which the second chamber includes a deformable sleeve disposed about the cylinder.

7. Catheter apparatus for the one-handed insertion of a catheter, confirmation of catheter insertion, and withdrawal of catheter insertion apparatus, comprising, in combination:
    catheter means, including
        a cannula having a tip for insertion into a vein,
        an intermediate portion connected to the cannular,
        a cylindrical portion connected to the intermediate portion and having an interior bore for receiving a needle for catheter insertion and for receiving a fluid connector after insertion,
        an upwardly extending shield on the cylindrical portion comprising a thumb rest for removing the needle after catheter insertion and confirmation of catheter insertion;
    catheter insertion means, including
        a hollow needle extending into and through the cylindrical portion, the intermediate portion, and the cannular of the catheter,
        a nose portion secured to the needle and extending into the bore of the cylindrical portion of the catheter,
        chamber means, including a fixed chamber connected to the needle for receiving a flow of blood from the vein to confirm catheter insertion into the vein;
        a movable chamber communicating with the fixed chamber for evacuating air from the fixed chamber and the movable chamber for enhancing the flow of blood into the fixed chamber, and
        valve means located in said chamber means for providing a one-way flow of blood into the fixed chamber and a one-way flow of air out of the movable chamber.

8. The apparatus of claim 7 in which the valve means comprises a first and a second one-way valve.

9. The apparatus of claim 8 in which the first one-way valve is disposed between the fixed chamber and the movable chamber.

10. The apparatus of claim 8 in which the first one-way valve is disposed between the hollow needle and the fixed chamber.

* * * * *